(12) United States Patent
Roecken et al.

(10) Patent No.: US 10,609,806 B2
(45) Date of Patent: Mar. 31, 2020

(54) ENERGY MODULATION OF A CYCLOTRON BEAM

(71) Applicant: Varian Medical Systems Particle Therapy GmbH, Troisdorf (DE)

(72) Inventors: Heinrich Roecken, Bonn (DE); Peter vom Stein, Overath (DE)

(73) Assignee: Varian Medical Systems Particle Therapy GmbH, Troisdorf (DE)

( * ) Notice: Subject to any disclaimer, the term of this patent is extended or adjusted under 35 U.S.C. 154(b) by 162 days.

(21) Appl. No.: 15/656,973

(22) Filed: Jul. 21, 2017

(65) Prior Publication Data
US 2019/0029101 A1  Jan. 24, 2019

(51) Int. Cl.
| H05H 7/12 | (2006.01) |
| H05H 7/00 | (2006.01) |
| A61N 5/10 | (2006.01) |
| H05H 13/00 | (2006.01) |

(52) U.S. Cl.
CPC ............. *H05H 7/12* (2013.01); *A61N 5/1043* (2013.01); *A61N 5/1077* (2013.01); *H05H 7/001* (2013.01); *A61N 2005/1087* (2013.01); *H05H 13/005* (2013.01); *H05H 2007/004* (2013.01); *H05H 2007/122* (2013.01); *H05H 2277/11* (2013.01)

(58) Field of Classification Search
CPC .......... A61N 5/1077; A61N 2005/1087; A61N 5/1043; H05H 7/001; H05H 7/12; H05H 2277/11; H05H 2007/004; H05H 2007/122; H05H 13/005
See application file for complete search history.

(56) References Cited

U.S. PATENT DOCUMENTS

| 5,834,787 A | 11/1998 | Bunker |
| 6,580,084 B1 | 6/2003 | Hiramoto et al. |
| 6,888,832 B2 | 5/2005 | Richardson et al. |
| 6,920,202 B1 | 7/2005 | Dinsmore |
| 7,423,278 B2 | 9/2008 | Amaldi et al. |
| 7,554,275 B2 | 6/2009 | Amaldi |
| 7,778,691 B2 | 8/2010 | Zhang et al. |

(Continued)

FOREIGN PATENT DOCUMENTS

| EP | 2108401 A1 | 11/2008 |
| EP | 2810693 A2 | 10/2014 |

(Continued)

OTHER PUBLICATIONS

H. Paganetti et al., "Proton Beam Radiotherapy—The State of the Art," New Technologies in Radiation Oncology (Medical Radiation Series), Springer Verlag, Heidelberg, ISBN 3-540-00321-5, Oct. 2005, 36 pages.

(Continued)

*Primary Examiner* — Christine H Matthews
*Assistant Examiner* — Joshua Daryl D Lannu

(57) ABSTRACT

In various embodiments, a radiation therapy system can include a cyclotron that outputs a charged particle beam. In addition, the radiation therapy system can include an apparatus to receive the charged particle beam from the cyclotron. The apparatus decelerates or further accelerates the charged particle beam to produce a reduced or increased energy charged particle beam. The apparatus can include a radio frequency structure.

20 Claims, 6 Drawing Sheets

(56) References Cited

U.S. PATENT DOCUMENTS

| | | | |
|---|---|---|---|
| 8,071,966 | B2 | 12/2011 | Kaiser et al. |
| 8,121,253 | B2 | 2/2012 | Nelms |
| 8,253,121 | B2 | 8/2012 | Gnutzmann et al. |
| 8,405,056 | B2 | 3/2013 | Amaldi et al. |
| 8,406,844 | B2 | 3/2013 | Ruchala et al. |
| 8,618,521 | B2 | 12/2013 | Loo et al. |
| 8,636,636 | B2 | 1/2014 | Shukla et al. |
| 8,644,571 | B1 | 2/2014 | Schulte et al. |
| 8,699,664 | B2 | 4/2014 | Otto et al. |
| 8,798,343 | B2 | 8/2014 | Kabus et al. |
| 8,901,519 | B2 | 12/2014 | Schardt et al. |
| 8,986,186 | B2 | 3/2015 | Zhang et al. |
| 9,018,603 | B2 | 4/2015 | Loo et al. |
| 9,033,859 | B2 | 5/2015 | Fieres et al. |
| 9,149,656 | B2 | 10/2015 | Tanabe |
| 9,636,525 | B1 | 5/2017 | Sahadevan |
| 2002/0030164 | A1 | 3/2002 | Akiyama et al. |
| 2002/0057760 | A1 | 5/2002 | Carroll et al. |
| 2006/0193435 | A1 | 8/2006 | Hara et al. |
| 2006/0274061 | A1 | 12/2006 | Wang et al. |
| 2007/0034812 | A1 | 2/2007 | Ma et al. |
| 2008/0049897 | A1 | 2/2008 | Molloy |
| 2008/0226030 | A1 | 9/2008 | Otto |
| 2009/0283702 | A1 | 11/2009 | Umezawa et al. |
| 2010/0003770 | A1 | 1/2010 | Shibata et al. |
| 2010/0195793 | A1 | 8/2010 | Nelms |
| 2010/0288945 | A1 | 11/2010 | Gnutzmann et al. |
| 2011/0006214 | A1* | 1/2011 | Bonig .............. H05H 7/18 250/396 R |
| 2011/0168903 | A1 | 7/2011 | Kyele et al. |
| 2012/0134470 | A1 | 5/2012 | Shibuya et al. |
| 2012/0136194 | A1 | 5/2012 | Zhang et al. |
| 2013/0172658 | A1* | 7/2013 | Brahme .............. A61N 5/1048 600/1 |
| 2014/0152176 | A1 | 6/2014 | Chang |
| 2014/0265823 | A1 | 9/2014 | Boisseau et al. |
| 2014/0270086 | A1 | 9/2014 | Krasnykh |
| 2015/0011817 | A1 | 1/2015 | Feng |
| 2015/0057484 | A1 | 2/2015 | Amaldi |
| 2015/0087882 | A1 | 3/2015 | Pausch et al. |
| 2015/0094838 | A1 | 4/2015 | Mac Laverty |
| 2015/0117616 | A1 | 4/2015 | Ishii et al. |
| 2015/0306423 | A1 | 10/2015 | Bharat et al. |
| 2016/0193482 | A1 | 7/2016 | Fahrig et al. |
| 2016/0225477 | A1 | 8/2016 | Banine et al. |
| 2016/0287905 | A1 | 10/2016 | Liger |
| 2016/0310764 | A1 | 10/2016 | Bharadwaj et al. |
| 2017/0028220 | A1 | 2/2017 | Schulte et al. |
| 2017/0203125 | A1 | 7/2017 | Amato et al. |
| 2018/0235554 | A1 | 8/2018 | Burgett |

FOREIGN PATENT DOCUMENTS

| | | |
|---|---|---|
| EP | 2805745 | 11/2014 |
| EP | 2979728 | 2/2016 |
| EP | 3043863 A1 | 7/2016 |
| EP | 3103519 A1 | 12/2016 |
| JP | 2014161706 A | 9/2014 |
| JP | 2017098000 A | 6/2017 |
| WO | 2006005059 | 12/2006 |
| WO | 2009042952 A1 | 4/2009 |
| WO | 2010088442 A1 | 8/2010 |
| WO | 2012135196 A1 | 10/2012 |
| WO | 2013038240 A1 | 3/2013 |
| WO | 2014139493 | 9/2014 |
| WO | 2015038832 A1 | 3/2015 |
| WO | 2015077881 A1 | 4/2015 |
| WO | 2015153746 A1 | 10/2015 |
| WO | 2016094284 A1 | 6/2016 |
| WO | 2016094284 A9 | 6/2016 |

OTHER PUBLICATIONS

Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-2405/2012/39(11)/7140/13, 13 pages.

Vincent Favuadon, Laura Caplier, Virginie Monceau, Frederic Pouzoulet, Mano Sayarath, Charles Fouillade, Marie-France Poupon, Isabel Brito, Philippe Hupe, Jean Bounhis,Janet Hall, Jean-Jacques Fontaine, Marie-Catherine Vozenin, vol. 6 Issue 245 245ra93, www.ScienceTranslationalMedicine.org, UltraHigh dose-rate FLASH irradiation increase4s the differential response between normal and tumor tissue in mice, 9 pages.

Valerie Devillaine, Radiotherapy and radiation biology, Radiotherapy—new treatment methods, Radio-toxicity, radio resistance and pediatric cancers, Photo-sensitization and retinoblastoma, 6 pages.

Radiotherapy "flashes" to reduce side effects, An effect for each mode of administration, Images of tissue sections, Ultra-high dose-rate, Science Translational Medicine, Jul. 16, 2014, 3 pages.

To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye—view as applied to beam orientation selection in intensity-modulated radiation therapy.

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-647 https://accelconf.web.cern.ch/accelconf/p01/PAPERS/FOAA004.PDF.

Th. Haberer,W. Becher,D. Schardt,G. Kraft "Magnetic scanning system for heavy ion therapy" Nuclear Instruments and Methods in Physics Research Section A: Accelerators, Spectrometers, Detectors and Associated Equipment , NIM , Elsevie, Jun. 10, 1993, vol. 330, Issues 1-2, Jun. 10, 1993, pp. 296-305.

Amaldi, TERA Foundation, Novara, Italy A. Degiovanni, Cern, Geneva, Switzerland Linac 2014. Proton and Carbon Linacs for Hadron Therapy U. http://accelconf.web.cern.ch/AccelConf/LINAC2014/papers/friob02.pdf. pp. 1207-1212.

Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: S0167-8140(17)30365-1. doi: 10.1016/j.radonc.2017.05.003. [Epub ahead of print] PubMed PMID: 28545957.

Favaudon V, Caplier L, Monceau V, Pouzoulet F, Sayarath M, Fouillade C, Poupon MF, Brito I, Hupé P, Bourhis J, Hall J, Fontaine JJ, Vozenin MC. Ultrahigh dose-rate Flash irradiation increases the differential response between normal and tumor tissue in mice. Sci Transl Med. Jul. 16, 2014;6(245):245ra93. doi: 10.1126/scitranslmed.3008973. PubMed PMID: 25031268.

Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics. vol. 98 Issue: 2 pp. E16-E16 Supplement: S Meeting Abstract: P003 Published: Jun. 1, 2017.

M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259.

K. Peach, et al. "Pamela—A Model for an FFAG Based Hadron Therapy Machine", Proceedings of PAC07, Albuquerque, New Mexico, USA. pp. 2880-2882.

S. Benedetti, A. Grudiev, and A. Latina Phys. Rev. Accel. Beams 20, 040101—Published Apr. 13, 2017.

(56) References Cited

OTHER PUBLICATIONS

Z. Li, et. al., Normal conducting cw transverse crab cavity for producing short pulses in spear3, Proceedings of IPAC2017, Copenhagen, Denmark. pp. 2840-2843.

Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, pp. 171501-171501-3, Oct. 2010. American Institute of Physics.

Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].

S. Tantawi, Z. Li, et al. patent pending, Title: "Distributed Coupling and Multi-Frequency Microwave Accelerators", Filed: Jul. 9, 2014, U.S. Appl. No. 62/022,469.

S. Tantawi, M.Nasr, "Designs and High Power Tests of Distributed Coupling Linacs" IFIC, Jun. 13-16, 2017, Valencia, Spainhttps://indico.cern.ch/event/589548/contributions/2615455/attachments/1479738/2294080/Mamdouh_High_Gradient_2017.pdf.

Jensen, Aaron, Jeff Neilson, and Sami Tantawi. "X-band multi-beam klystron design and progress report." Vacuum Electronics Conference (IVEC), 2015 IEEE International. IEEE, 2015.

K.Halbach, "Design of permanent multipole magnets with oriented rare earth cobalt material", Nuclear Instruments and Methods, vol. 169, Issue 1, Feb. 1, 1980, pp. 1-12 [http://www.sciencedirect.com/science/article/pii/0029554X80900944].

J. K. Lim, P. Frigola, G. Travish, J. B. Rosenzweig, S. G. Anderson, W. J. Brown, J. S. Jacob, C. L. Robbins, and A. M. Tremaine, "An Adjustable, short focal length permanent-magnet quadrupole based electron beam final focus system" Phys. Rev. ST Accel. Beams 8, 072401—Published Jul. 15, 2005. 19 pages.

Sayyed Bijan Jiaa, Mohammad Hadi Hadizadeha, Ali Asghar Mowlavi, Mahdy Ebrahimi Loushab "Evaluation of energy deposition and secondary particle production in proton therapy of brain using a slab head phantom" Elsevier, Reports of Practical Oncology & Radiotherapy,vol. 19, Issue 6, Nov.-Dec. 2014, pp. 376-384.

J.Perl, J Shin, J Schümann, B Faddegon and H Paganetti, "TOPAS—An innovative proton Monte Carlo platform for research and clinical applications," Med. Phys. 39:6818-6837, 2012, PMID: 23127075, PMID: 23127075.

Lisa Polster, Jan Schuemann, Ilaria Rinaldi, Lucas Burigo, Aimee Louise McNamara, Robert D Stewart, Andrea Attili, David J. Carlson, Alejandro Carabe-Fernadez, Bruce Faddegon, Joseph Perl, and Harald Paganetti, "Extension of TOPAS for the simulation of proton radiation on molecular and cellular endpoints," Phys Med Biol. Jun. 10, 2015;60(13):5053-5070, PMID: 26061583.

Schuler, Emil, et al. "Experimental platform for ultra-high does rate FLASH irradiation of small animals using a clinical linear accelerator." International Journal of Radiation Oncology*Biology*Physics, vol. 97, No. 1, 2017, pp. 195-203.

J. Amaldi et al., "Cyclinacs: Fast-Cycling Accelerators for Hadrontherapy," Nuclear Inst. and Methods in Physics Research, Mar. 2009.

S. Verdú-Andrés et al., "Caboto, a high-gradient linac for hadrontherapy," Journal of Radiation Research, 2013, 54, pp. i155-i161.

A. Degiovanni et al., "Design of a Fast-Cycling High-Gradient Rotating Linac for Protontherapy," Proceedings of IPAC2013, Shanghai, China, THPWA008, 2013, pp. 3642-3644.

S. Verdú-Andrés et al., "Feasibility Study of a High-Gradient Linac for Hadrontherapy," Proceedings of IPAC2011, San Sebastián, Spain, WEPS045, 2011, pp. 2589-2591.

\* cited by examiner

ENERGY MODULATION OF A CYCLOTRON BEAM

BACKGROUND

The use of radiation therapy to treat cancer is well known. Typically, radiation therapy involves directing a beam of high energy proton, photon, ion, or electron radiation ("therapeutic radiation") into a target or target volume (e.g., a tumor or lesion) in a patient.

It is noted that cyclotrons are the most cost efficient particle accelerators for state of the art particle therapy. Cyclotrons are fixed energy accelerators and require a beam degrader for energy modulation of the treatment beam. However, there are disadvantages associated with cyclotrons.

For example, degraders have the disadvantage that they only provide relatively slow energy modulation in the range of several 100 ms (milliseconds) and feature high beam losses, which inevitably lead to large neutron generation requiring costly radiation shielding.

SUMMARY

Various embodiments in accordance with the present disclosure can address the disadvantages described above.

In various embodiments, the present disclosure includes a combination of a cyclotron with a linear accelerator/decelerator in order to achieve fast energy modulation without high beam loss for the purpose of particle therapy. The cyclotron can be optimized for a substantially fixed energy charged particle beam at approximately (or substantially) the medium or middle of the desired treatment energy range. The subsequent linear accelerator/decelerator acts as post accelerator or decelerator including a high gradient radio frequency (RF) structure allowing further beam acceleration or deceleration to cover the whole desired energy range for particle therapy.

In various embodiments, it is noted that the combination of the cyclotron and linear accelerator/decelerator provides the desirable results of very fast energy modulation with very low beam loss. Therefore, this yields different advantages over the conventional cyclotron and degrader combination, but is not limited to such. One advantage is that it results in fast energy switching. Another advantage is that high beam intensity is possible for all desired energies (e.g., in one or more pulses of order 10 microseconds (μs) duration, with a repetition rate on the order of 100 pulses/second). Yet another advantage is that a reduced amount of radiation shielding can be implemented as part of the treatment system. It is pointed out that high instantaneous beam current (in a pulse) and fast energy switching possibly allows for advanced therapy applications, like 3D (three-dimensional) repainting (e.g., uniform in-depth dose distribution) or ultra-short dose delivery times.

In various embodiments, a radiation therapy system can include a cyclotron that outputs a charged particle beam. In addition, the radiation therapy system can include an apparatus to receive the charged particle beam from the cyclotron. The apparatus decelerates or further accelerates the charged particle beam to produce a reduced or increased energy charged particle beam. The apparatus can include a radio frequency structure.

In various embodiments, a radiation therapy system can include a cyclotron that outputs a charged particle beam. In addition, the radiation therapy system can include an apparatus to receive the charged particle beam from the cyclotron. The apparatus decelerates the charged particle beam to produce a reduced energy charged particle beam. The apparatus can include a radio frequency structure.

In various embodiments, a method can include a cyclotron generating a charged particle beam. Furthermore, the method can include an apparatus decelerating the charged particle beam to produce a reduced energy charged particle beam. The apparatus can include a radio frequency structure.

In various embodiments, a radiation therapy system can include a cyclotron that outputs a substantially fixed energy charged particle beam. The radiation therapy system can also include an apparatus to receive the substantially fixed energy charged particle beam from the cyclotron. The apparatus decelerates or accelerates the substantially fixed energy charged particle beam to produce a reduced or increased energy charged particle beam. The apparatus can include a radio frequency structure.

While various embodiments in accordance with the present disclosure have been specifically described within this Summary, it is noted that the claimed subject matter are not limited in any way by these various embodiments.

BRIEF DESCRIPTION OF THE DRAWINGS

Within the accompanying drawings, various embodiments in accordance with the present disclosure are illustrated by way of example and not by way of limitation. It is noted that like reference numerals denote similar elements throughout the drawings.

DETAILED DESCRIPTION

Figure 1:
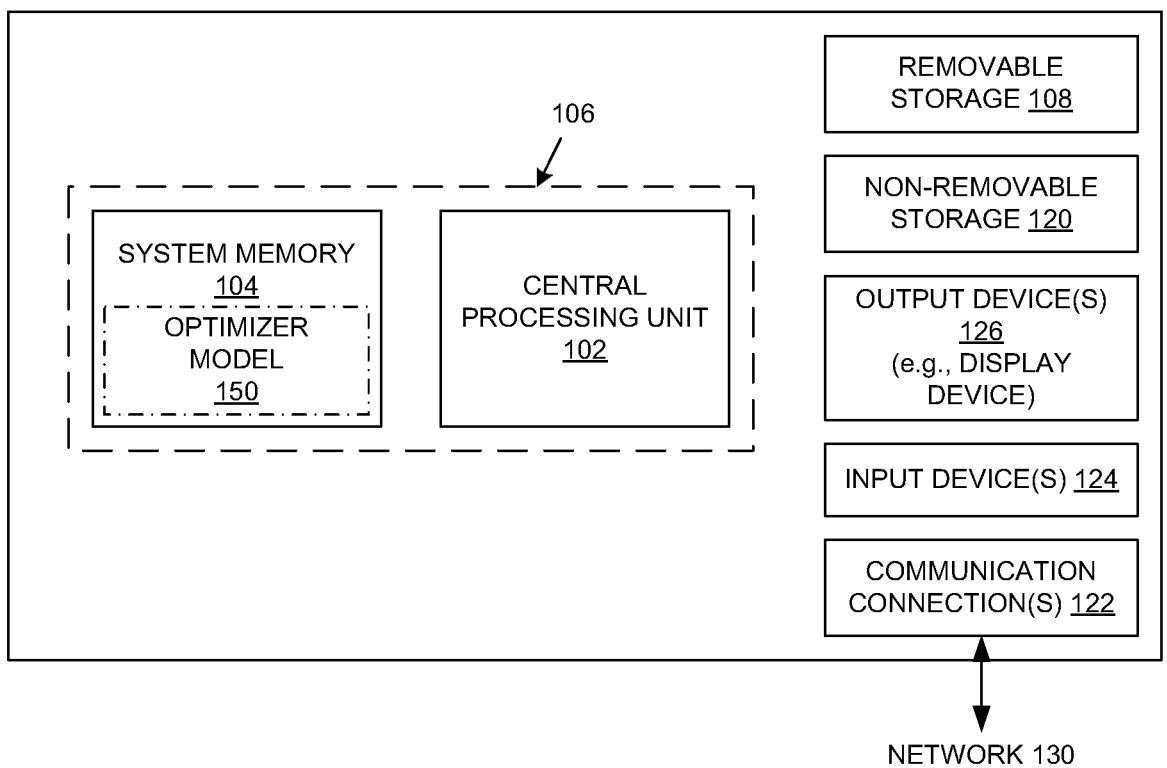
FIG. 1 is a block diagram of an example of a computing system upon which various embodiments described herein may be implemented in accordance with various embodiments of the present disclosure.

Reference will now be made in detail to various embodiments in accordance with the present disclosure, examples of which are illustrated in the accompanying drawings. While described in conjunction with various embodiments, it will be understood that these various embodiments are not intended to limit the present disclosure. On the contrary, the present disclosure is intended to cover alternatives, modifications and equivalents, which may be included within the scope of the present disclosure as construed according to the Claims. Furthermore, in the following detailed description of various embodiments in accordance with the present disclosure, numerous specific details are set forth in order to provide a thorough understanding of the present disclosure. However, it will be evident to one of ordinary skill in the art that the present disclosure may be practiced without these specific details or with equivalents thereof. In other instances, well known methods, procedures, components, and circuits have not been described in detail as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," "acquiring," "triggering", "computing", "loading" or the like, refer to actions and processes of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein describing the operations of this method, such steps and sequencing are exemplary. Any method is well suited to performing various other steps or variations of the steps recited in the flowchart of the figure herein, and in a sequence other than that depicted and described herein.

Various embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which various embodiments described herein may be implemented in accordance with various embodiments of the present disclosure. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment 130 using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 in accordance with various embodiments is described below.

It is noted that the computing system 100 may not include all of the elements illustrated by FIG. 1. In addition, the computing system 100 can be implemented to include one or more elements not illustrated by FIG. 1. It is pointed out that the computing system 100 can be utilized or implemented in any manner similar to that described and/or shown by the present disclosure, but is not limited to such.

Figure 2:
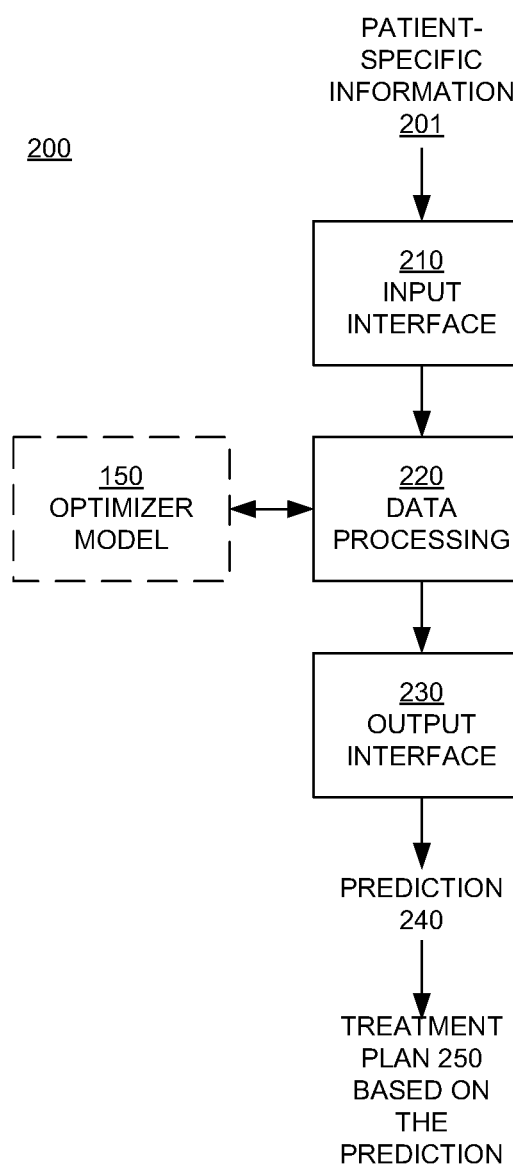
FIG. 2 is a block diagram illustrating an example of an automated radiation therapy treatment planning system in accordance with various embodiments of the present disclosure.

FIG. 2 is a block diagram illustrating an example of an automated radiation therapy treatment planning system 200 in accordance with various embodiments of the present disclosure. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computing system 100 (FIG. 1).

In the example of FIG. 2, the patient-specific information is provided to and processed by the optimizer model 150. The optimizer model 150 yields a prediction result 240. A treatment plan 250 based on the prediction result 240 can then be generated. It is pointed out that the treatment plan 250 can be personalized for a human patient and can include the type of radiation therapy to implement and dose distribution. The optimizer model 150 can provide, for example, a three-dimensional (3D) dose distribution, fluences, and associated dose-volume histograms for the current patient, but is not limited to such.

Note that the system 200 may not include all of the elements illustrated by FIG. 2. Furthermore, the system 200 can be implemented to include one or more elements not illustrated by FIG. 2. It is pointed out that the system 200 can be utilized or implemented in any manner similar to that described and/or shown by the present disclosure, but is not limited to such.

Figure 3A:
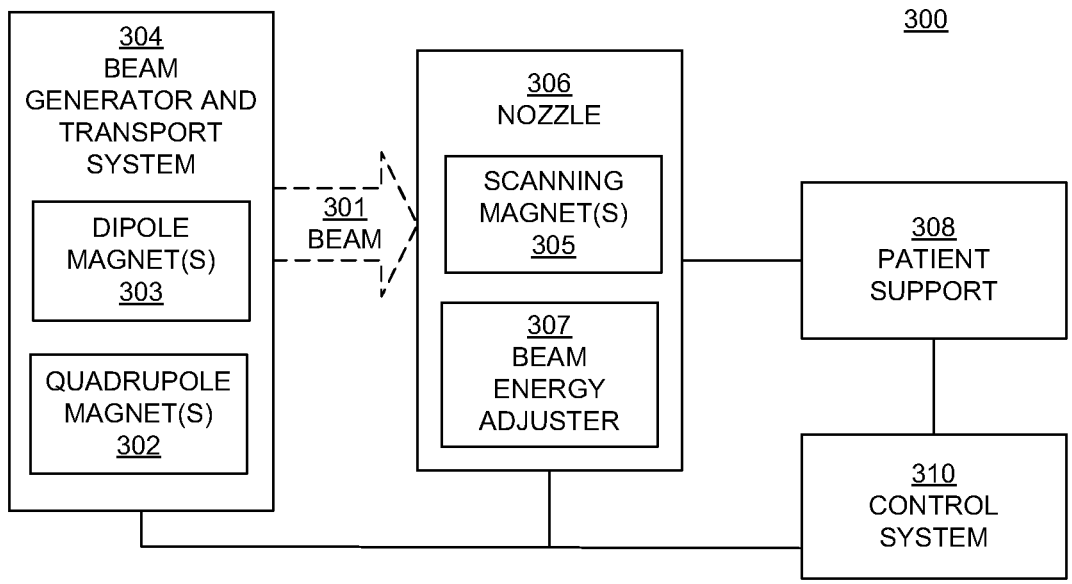
FIG. 3A is a block diagram showing selected components of a radiation therapy system in accordance with various embodiments of the present disclosure.

FIG. 3A is a block diagram showing selected components of a radiation therapy system 300 in accordance with various embodiments of the present disclosure. In the example of FIG. 3A, the system 300 includes a particle beam generator and transport system 304 and a nozzle 306.

The beam generator and transport system 304 generates a charged particle beam of, but not limited to, protons, carbon ions, alpha particles, or helium nuclei, and contains the particles in a well-defined beam. In various embodiments, the beam generator 304 can produce a continuous wave output beam or pulsed output beams, but is not limited to such. In addition, the beam generator 304 can output (or emit or generate) particles with a specified energy. In various embodiments, the beam generator 304 can produce a charged particle beam within the range of 70-300 million electron volts (MeV), but is not limited to such.

Within FIG. 3A, in various embodiments, the beam generator and transport system 304 can include components (e.g., dipole magnets 303 and quadrupole magnets 302) that bend and focus the beam through the beam generator and transport system 304 in a direction toward and into the nozzle 306. Specifically, in various embodiments, the dipole magnets 303 can be utilized for bending the beam while the quadrupole magnets 302 can be utilized for focusing the beam. In various embodiments, note that the beam generator and transport system 304 may be implemented to include, but is not limited to, steering magnets (not shown) that can be utilized for correcting beam direction and/or solenoid magnets (not shown) that can be utilized for focusing the beam. In various embodiments, the beam generator and transport system 304 may also include a beam energy adjuster 307 (described below) that is used to further adjust the beam energy entering the nozzle 306, but is not limited to such.

In various embodiments, the nozzle 306 is used to aim the beam toward various locations (e.g., a target) within an object (e.g., a human patient) supported on the patient support device 308 (e.g., a chair or table) in a treatment room. A target may be an organ, a portion of an organ (e.g., a volume or region within the organ), a tumor, diseased tissue, or a patient outline. In various embodiments, the nozzle 306 also includes components (e.g., scanning magnets 305) that steer (e.g., guide, deflect, or scan) the beam particles substantially perpendicular to the beam direction, to scan a target in a patient on the patient support device 308. In various embodiments, the nozzle 306 may also include one or more multileaf collimators (MLCs); each MLC leaf can be independently moved back-and-forth by the control system 310 to dynamically shape an aperture through which the beam can pass, to block or not block portions of the beam and thereby control beam shape and exposure time. Note that in various embodiments, the nozzle 306 may include one or more MLCs instead of the scanning magnets 305.

Within FIG. 3A, the nozzle 306 may be mounted on or a part of a gantry (e.g., FIGS. 3B, 3C, and 3D) that can be moved relative to the patient support device 308, which may also be moveable. In various embodiments, the beam generator and transport system 304 is also mounted on or is a part of the gantry; in various embodiments, the beam generator and transport system 304 is separate from (but in communication with) the gantry.

In various embodiments, the control system 310 of FIG. 3A receives and implements a prescribed treatment plan. In various embodiments, the control system 310 includes a computer system having a processor, memory, an input device (e.g., a keyboard), and perhaps a display in well-known fashion. The control system 310 can receive data regarding operation of the system 300. The control system 310 can control parameters of the beam generator and transport system 304, nozzle 306, and patient support device 308, including parameters such as the energy, intensity, direction, size, and/or shape of the beam, according to data it receives and according to the prescribed treatment plan.

Within FIG. 3A, the particles entering the nozzle 306 have a specified energy. Thus, in various embodiments according to the present disclosure, the nozzle 306 can include one or more components that affect (e.g., decrease, modulate) the energy of the particles in the beam 301. The term "beam energy adjuster" is used herein as a general term for a component or components that affect the energy of the particles in the beam, in order to control the range of the beam (e.g., the extent that the beam penetrates into a target) and/or to control the depth dose curve of the beam (e.g., the location of the Bragg peak in the target). In various embodiments, the beam energy adjuster 307 includes a range modulator, a range shifter, or both a range modulator and a range shifter. That is, when the term "beam energy adjuster" is used, then the element being discussed may be a range modulator, a range shifter, or both a range modulator and a range shifter. Examples of a beam energy adjuster are disclosed in the co-pending patent application, U.S. application Ser. No. 15/089,330, now U.S. Pat. No. 9,855,445, entitled "Radiation Therapy Systems and Methods for Delivering Doses to a Target Volume"; however, the present disclosure is not so limited.

Note that the system 300 may not include all of the elements illustrated by FIG. 3A. In addition, the system 300 can be implemented to include one or more elements not illustrated by FIG. 3A. It is pointed out that the system 300 can be utilized or implemented in any manner similar to that described and/or shown by the present disclosure, but is not limited to such.

Figure 3B:
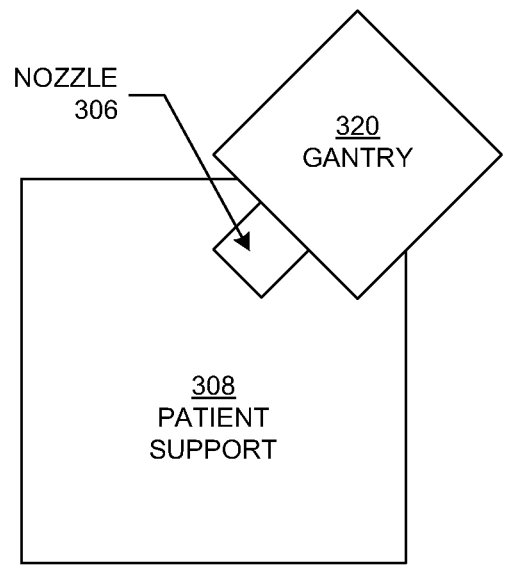
FIG. 3B is a block diagram illustrating a non-coplanar arrangement of a gantry and nozzle relative to a patient support device in accordance with various embodiments of the present disclosure.
Figure 3C:
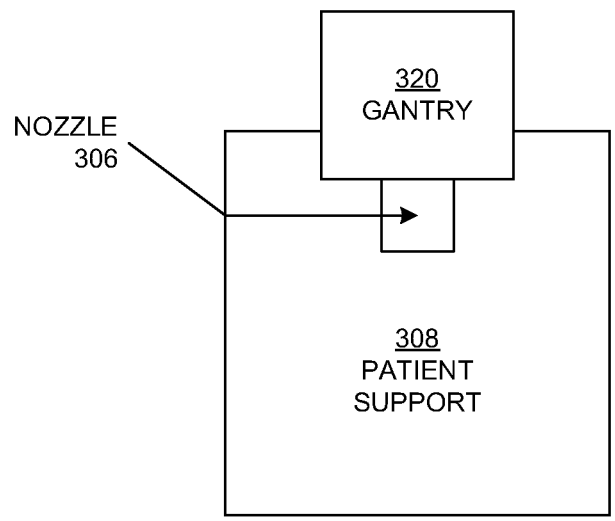
FIG. 3C is a block diagram illustrating a coplanar arrangement of a gantry and nozzle relative to a patient support device in accordance with various embodiments of the present disclosure.
Figure 3D:
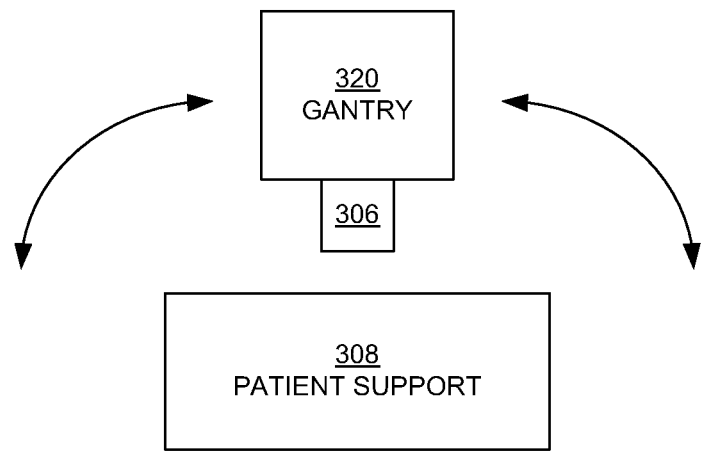
FIG. 3D is a block diagram illustrating movement of a gantry and nozzle around a patient support device in accordance with various embodiments of the present disclosure.

FIG. 3B is a block diagram illustrating a non-coplanar arrangement of a gantry 320 and nozzle 306 relative to a patient support device 308 in accordance with various embodiments of the present disclosure. FIG. 3C is a block diagram illustrating a coplanar arrangement of a gantry 320 and nozzle 306 relative to a patient support device 308 in accordance with various embodiments of the present disclosure. FIG. 3D is a block diagram illustrating movement of the gantry 320 and nozzle 306 around the patient support device 308 in accordance with various embodiments of the present disclosure. It is pointed out that this movement can occur in either the non-coplanar arrangement or the coplanar arrangement.

Figure 4:
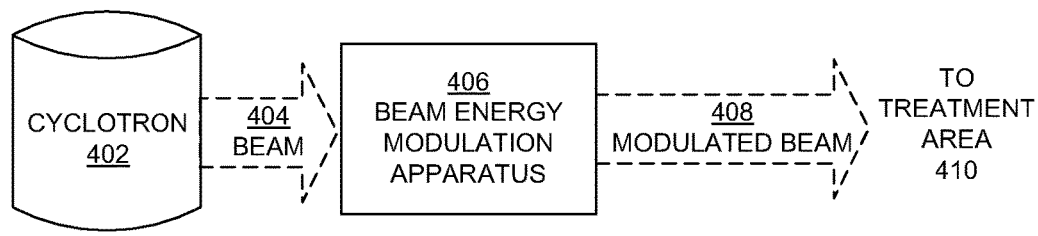
FIG. 4 is a block diagram illustrating a beam generator and transport system in accordance with various embodiments of the present disclosure.

FIG. 4 is a block diagram illustrating a beam generator and transport system 400 in accordance with various embodiments of the present disclosure. It is noted that in various embodiments, the beam generator and transport system 400 can be utilized to implement the beam generator and transport system 304 of FIG. 3, but is not limited to such. Within FIG. 4, the beam generator and transport system 400 can include a combination of a cyclotron 402 with a beam energy modulation apparatus 406 in order to achieve fast energy modulation without high beam loss for the purpose of particle therapy. In various embodiments, the cyclotron 402 can be optimized to generate a substantially fixed energy charged particle beam 404 at approximately (or substantially) the medium or middle of the desired treatment energy range. In addition, the subsequent beam energy modulation apparatus 406 acts as post accelerator or decelerator that can include a high gradient radio frequency (RF) structure allowing further beam acceleration or deceleration to cover the whole desired energy range for particle therapy.

Note that the beam energy modulation apparatus 406 can be implemented in a wide variety of ways in accordance with various embodiments. For example, in various embodiments, the beam energy modulation apparatus 406 can be implemented with a linear accelerator/decelerator that can include several sequential RF structures. In various embodiments, the RF structures can operate with rapid alternating voltages. In addition, the phase of these alternating voltages can be changed with respect to the incoming charged particle beam 404 in order to accelerate or decelerate the charged particle beam 404. Therefore, the RF structures can electrically operate in a first phase mode to accelerate the charged particle beam 404, or in another phase mode to decelerate the charged particle beam 404, but are not limited to such. In various embodiments, the RF structures can be optimized for high shunt impedance enabling operation at high accelerating gradients with high duty factor (e.g., coupled cavity linear accelerator/decelerator structures or traveling wave structures). In various embodiments, it is understood that the shunt impedance measures the efficiency of an accelerating (or decelerating) structure, which is the ratio between the square of accelerating (or decelerating) voltage over the absorbed RF power (e.g., $R=U_{acc}^2/P_{RF}$). An RF structure with high shunt impedance enables higher RF voltages (e.g., high accelerating gradients) for particle acceleration/deceleration with longer pulses (e.g., high duty factor), which is equivalent to higher achievable average beam current. In various embodiments, the RF structures can be implemented to consume little energy while generating high electric fields resulting in an efficient accelerating or decelerating structure.

Within FIG. 4, it is pointed out that the combination of the cyclotron 402 and the beam energy modulation apparatus 406 can provide the desirable results of very fast energy modulation with very low beam loss. Therefore, this yields different advantages over the conventional cyclotron and degrader combination, but is not limited by such. One advantage is that it results in very fast energy switching. Another advantage is that high beam intensity is possible for all desired energies (e.g., in one or more pulses of order 10 microseconds (μs) duration, with a repetition rate on the order of 100 pulses/second). Yet another advantage is that a reduced amount of radiation shielding can be implemented as part of the treatment system. Note that high instantaneous beam current (e.g., in a pulse) 408 and fast energy switching possibly allows for advanced therapy applications, like 3D (three-dimensional) repainting (e.g., uniform in-depth dose distribution) or ultra-short dose delivery times (e.g., less than 100 microseconds). In various embodiments, it is noted that the combination of accelerating and decelerating RF structures in the beam energy modulation apparatus 406 starting from an approximately (or substantially) medium or middle beam energy as provided by the cyclotron 402 has the potential to use just one type of RF structure, which may be more compact and cost effective than starting the beam energy modulation apparatus 406 right from low energy.

In various embodiments, the beam generator and transport system 400 can be utilized to deliver a dose of radiation therapy to a target volume within a fraction of a second (e.g., less than a second). In various embodiments, the beam generator and transport system 400 can be utilized to deliver the entire treatment dosage of radiation therapy to the target volume within a fraction of a second (e.g., less than a second). In addition, in various embodiments, the beam generator and transport system 400 can be utilized to deliver a fraction of the treatment dosage of radiation therapy to the target volume within a fraction of a second (e.g., less than a second). In various embodiments, each beam of the beam generator and transport system 400 can deliver a relatively high dose in a relatively short period of time. For example, each beam output by the beam generator and transport system 400 can deliver at least four (4) grays (Gy) in less than one second (sec), and may deliver as much as 20 Gy or 50 Gy or more in less than one second, but is not limited to such. In various embodiments, each beam output by the beam generator and transport system 400 can deliver, but is not limited to, greater than 4 Gy/sec, greater than 20 Gy/sec, or greater than 40 Gy/sec. In various embodiments, each beam output by the beam generator and transport system 400 can deliver, but is not limited to, at least 1 Gy in 0.25 sec, at least 1 Gy in 0.05 sec, or at least 1 Gy in 0.025 sec.

Within FIG. 4, the beam energy modulation apparatus 406 is based on an acceleration/deceleration structure optimized to the final output energy beam 404 of the cyclotron 402. The beam generator and transport system 400 can be utilized in a wide variety of ways in accordance with various embodiments of the present disclosure. For example, in various embodiments, the beam generator and transport system 400 can be utilized when the whole desired energy variation range is in the range of several 10 MeV, but is not limited to such.

In various embodiments, the cyclotron 402 can be implemented in a wide variety of ways. For example, in various embodiments, the cyclotron 402 can be an isochronous cyclotron capable of producing a continuous wave output beam or pulsed output beams, but is not limited to such. The cyclotron 402 can output (or emit or generate) particles with a specified energy. Furthermore, in various embodiments, the cyclotron 402 can be implemented as a lower power output cyclotron, such as a cyclotron that accelerates particles to the range of 70-300 million electron volts (MeV), but is not limited to such. In various embodiments, the cyclotron 402 can generate a charged particle beam 404 of, but not limited to, protons, carbon ions, alpha particles, or helium nuclei, and contains the particles in a well-defined beam.

Within the beam generator and transport system 400 of FIG. 4, the cyclotron 402 can generate and output a substantially fixed energy charged particle beam 404. The beam energy modulation apparatus 406 can be coupled with the cyclotron 402 in order to receive the charged particle beam 404. Depending on the data or instructions the beam energy modulation apparatus 406 receives from the control system (e.g., 310), the beam energy modulation apparatus 406 can accelerate or decelerate the received energy charged particle beam 404 to produce a modulated energy charged particle beam 408. It is noted that the modulated energy charged particle beam 408 can be output from the beam generator and transport system 400 to a treatment area 410 in order to be utilized for particle therapy (e.g., as described herein). In various embodiments, the output modulated energy charged particle beam 408 can be received by a nozzle (e.g., 306).

In various embodiments, a control system (e.g., 310) can be coupled to the cyclotron 402 and the beam energy modulation apparatus 406 in order to control their function and/or operation.

It is noted that the beam generator and transport system 400 may not include all of the elements illustrated by FIG. 4. Furthermore, the beam generator and transport system 400 can be implemented to include one or more elements not illustrated by FIG. 4. Note that the beam generator and transport system 400 can be utilized or implemented in any manner similar to that described and/or shown by the present disclosure, but is not limited to such.

Figure 5:
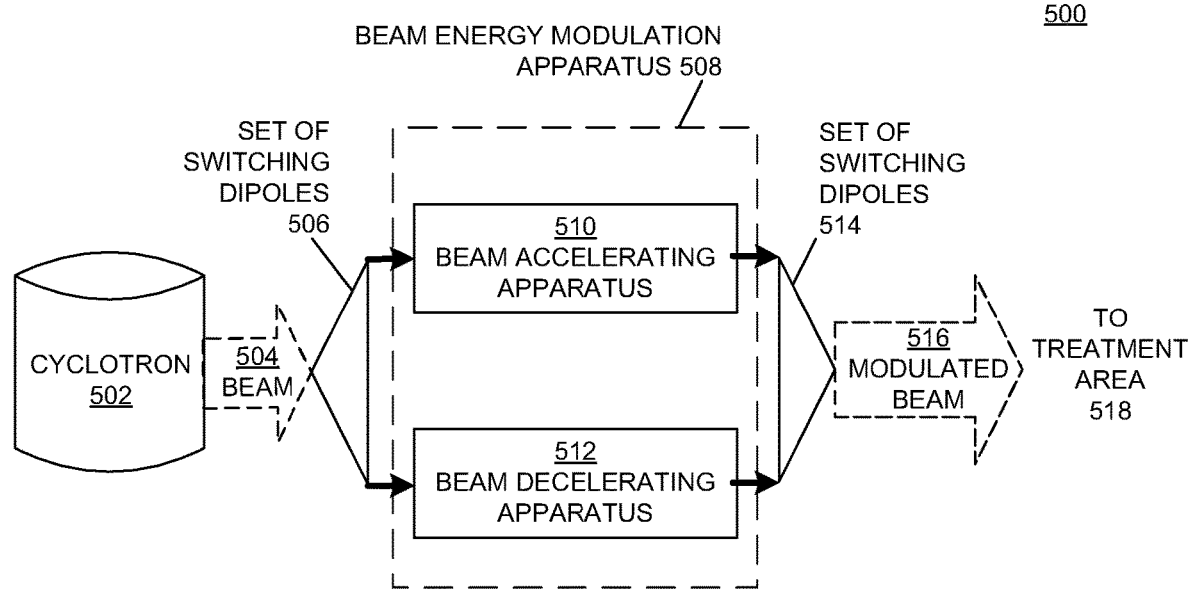
FIG. 5 is a block diagram illustrating a beam generator and transport system in accordance with various embodiments of the present disclosure.

FIG. 5 is a block diagram illustrating a beam generator and transport system 500 in accordance with various embodiments of the present disclosure. Note that in various embodiments, the beam generator and transport system 500 can be utilized to implement the beam generator and transport system 304 of FIG. 3, but is not limited to such. Within FIG. 5, the beam generator and transport system 500 can include, among other components, a combination of a cyclotron 502 with a beam energy modulation apparatus 508 in order to achieve fast energy modulation without high beam loss for the purpose of particle therapy. In various embodiments, the cyclotron 502 can be optimized to generate a substantially fixed energy charged particle beam 504 at approximately (or substantially) the medium or middle of the desired treatment energy range. Moreover, the subsequent beam energy modulation apparatus 508 acts as post accelerator or decelerator that can include a high gradient RF structure allowing further beam acceleration or deceleration to cover the whole desired energy range for particle therapy.

In various embodiments, it is pointed out that the cyclotron 502 can operate and/or be implemented in any manner similar to the cyclotron 402 of FIG. 4 as described and/or shown by the present disclosure, but is not limited to such.

Within FIG. 5, the beam energy modulation apparatus 508 can be implemented in a wide variety of ways in accordance with various embodiments. For example, in various embodiments, the beam energy modulation apparatus 508 can include a beam accelerating apparatus 510 and a beam decelerating apparatus 512. Therefore, a set of switching dipoles 506 can be coupled with the cyclotron 502 in order to receive the charged particle beam 504 and direct the charged particle beam 504 to either the input of the beam accelerating apparatus 510 or the input of the beam decelerating apparatus 512. In various embodiments, the beam accelerating apparatus 510 can be optimized to accelerate the charged particle beam 504 while the beam decelerating apparatus 512 can be optimized to decelerate the charged particle beam 504. A set of switching dipoles 514 can be coupled with the output of the beam accelerating apparatus 510 and the output of the beam decelerating apparatus 512 in order to receive a modulated energy charged particle beam 516 and direct it to be output from the beam generator and transport system 500 to a treatment area 518 to be utilized for particle therapy (e.g., as described herein). In various embodiments, the output modulated energy charged particle beam 516 can be received by a nozzle (e.g., 306).

In various embodiments, the beam accelerating apparatus 510 can be implemented with a linear accelerator that can include several sequential RF structures, which can operate with rapid alternating voltages. In various embodiments, the RF structures of the beam accelerating apparatus 510 can be optimized for high shunt impedance enabling operation at high accelerating gradients with high duty factor (e.g., coupled cavity linear accelerator structures or traveling wave structures). In various embodiments, the beam decelerating apparatus 512 can be implemented with a linear decelerator that can include several sequential RF structures, which can operate with rapid alternating voltages. In various embodiments, the RF structures of the beam decelerating apparatus 512 can be optimized for high shunt impedance enabling operation at high accelerating gradients with high duty factor (e.g., coupled cavity linear decelerator structures or traveling wave structures). In various embodiments, note that the phases of the alternating voltages in the RF structures of the beam decelerating apparatus 512 are different from the phases of the alternating voltages in the RF structures of the beam accelerating apparatus 510, but are not limited to such. In various embodiments, it is understood that the shunt impedance measures the efficiency of an accelerating (or decelerating) structure, which is the ratio between the square of accelerating (or decelerating) voltage over the absorbed RF power (e.g., $R=U_{acc}^2/P_{RF}$). An RF structure with high shunt impedance enables higher RF voltages (e.g., high accelerating gradients) for particle acceleration/deceleration with longer pulses (e.g., high duty factor), which is equivalent to higher achievable average beam current. In various embodiments, the RF structures of the beam accelerating apparatus 510 and the beam decelerating apparatus 512 can be implemented to consume little energy while generating high electric fields resulting in an efficient accelerating or decelerating structure.

Within FIG. 5, the combination of the cyclotron 502 and the beam energy modulation apparatus 508 can provide the desirable results of very fast energy modulation with very low beam loss. Consequently, this yields different advantages over the conventional cyclotron and degrader combination, but is not limited to such. One advantage is that it results in very fast energy switching. Another advantage is that high beam intensity is possible for all desired energies (e.g., in one or more pulses of order 10 microseconds (µs) duration, with a repetition rate on the order of 100 pulses/second). Yet another advantage is that a reduced amount of radiation shielding can be implemented as part of the treatment system. It is pointed out that high instantaneous beam current (e.g., in a pulse) 516 and fast energy switching possibly allows for advanced therapy applications, like 3D repainting (e.g., uniform in-depth dose distribution) or ultra-short dose delivery times (e.g., less than 100 microseconds).

In various embodiments, the beam generator and transport system 500 can be utilized to deliver a dose of radiation therapy to a target volume within a fraction of a second (e.g., less than a second). In various embodiments, the beam generator and transport system 500 can be utilized to deliver the entire treatment dosage of radiation therapy to the target volume within a fraction of a second (e.g., less than a second). Moreover, in various embodiments, the beam generator and transport system 500 can be utilized to deliver a fraction of the treatment dosage of radiation therapy to the target volume within a fraction of a second (e.g., less than a second). In various embodiments, each beam of the beam generator and transport system 500 can deliver a relatively high dose in a relatively short period of time. For example, each beam output by the beam generator and transport system 500 can deliver at least four (4) Gy in less than one second, and may deliver as much as 20 Gy or 50 Gy or more in less than one second (sec), but is not limited to such. In various embodiments, each beam output by the beam generator and transport system 500 can deliver, but is not limited to, greater than 4 Gy/sec, greater than 20 Gy/sec, or greater than 40 Gy/sec. In various embodiments, each beam output by the beam generator and transport system 500 can deliver, but is not limited to, at least 1 Gy in 0.25 sec, at least 1 Gy in 0.05 sec, or at least 1 Gy in 0.025 sec.

Within FIG. 5, the beam energy modulation apparatus 508 is based on the beam accelerating apparatus 510 and the beam decelerating apparatus 512 each being optimized to the final output energy charged particle beam 504 of the cyclotron 502. The beam generator and transport system 500 can be utilized in a wide variety of ways in accordance with various embodiments of the present disclosure. For example, in various embodiments, the beam generator and transport system 500 can be utilized for higher energy variation ranges (e.g., substantially 60 MeV or greater), but is not limited to such. In various embodiments, it is noted that the beam accelerating apparatus 510 and the beam decelerating apparatus 512 are arranged in a parallel configuration.

Within the beam generator and transport system 500 of FIG. 5, the cyclotron 502 can generate and output a substantially fixed energy charged particle beam 504 of, but not limited to, protons, carbon ions, alpha particles, or helium nuclei, and contains the particles in a well-defined beam. Depending on the data or instructions the set of switching dipoles 506 receive from the control system (e.g., 310), the set of switching dipoles 506 can direct the charged particle beam 504 to either the input of the beam accelerating apparatus 510 or the input of the beam decelerating apparatus 512 of the beam energy modulation apparatus 508. If the charged particle beam 504 is directed to the input of the beam accelerating apparatus 510, the beam accelerating apparatus 510 can accelerate the received energy charged particle beam 504 to produce a modulated energy charged particle beam 516 to the set of switching dipoles 514.

Alternatively, if the charged particle beam 504 is directed to the input of the beam decelerating apparatus 512, the beam decelerating apparatus 512 can decelerate the received energy charged particle beam 504 to produce a modulated energy charged particle beam 516 to the set of switching dipoles 514. Depending on the data or instructions the set of switching dipoles 514 receive from the control system (e.g., 310), the set of switching dipoles 514 can direct the modulated energy charged particle beam 516 to be output from the beam generator and transport system 500 to a treatment area 518 to be utilized for particle therapy (e.g., as described herein). In various embodiments, the output modulated energy charged particle beam 516 can be received by a nozzle (e.g., 306).

In various embodiments, a control system (e.g., 310) can be coupled to the cyclotron 502, sets of switching dipoles 506 and 514, beam energy modulation apparatus 508, beam accelerating apparatus 510, and beam decelerating apparatus 512 in order to control their function and/or operation.

Note that the beam generator and transport system 500 may not include all of the elements illustrated by FIG. 5. Additionally, the beam generator and transport system 500 can be implemented to include one or more elements not illustrated by FIG. 5. It is noted that the beam generator and transport system 500 can be utilized or implemented in any manner similar to that described and/or shown by the present disclosure, but is not limited to such.

Figure 6:
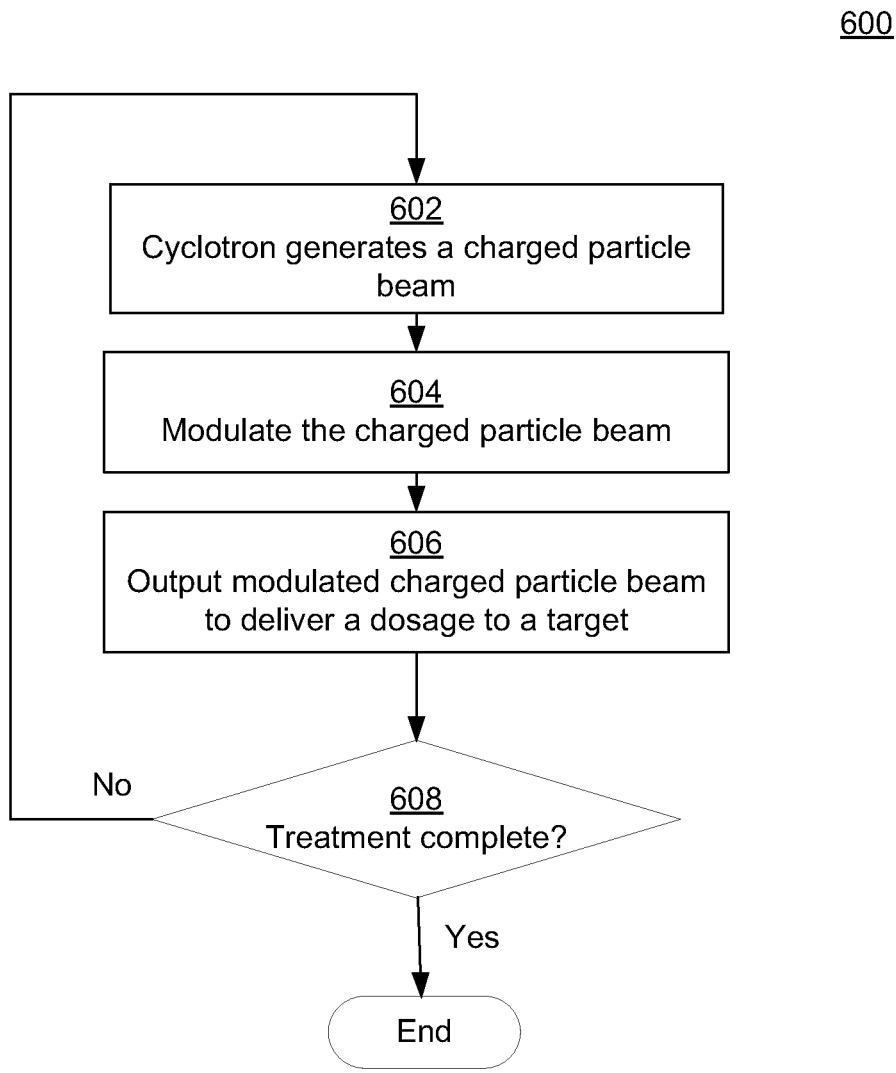
FIG. 6 is a flow diagram of a method in accordance with various embodiments of the present disclosure.

FIG. 6 is a flow diagram of a method 600 for performing energy modulation of a cyclotron beam for radiation therapy in accordance with various embodiments of the present disclosure. Although specific operations are disclosed in FIG. 6, such operations are examples. The method 600 may not include all of the operations illustrated by FIG. 6. Also, method 600 may include various other operations and/or variations of the operations shown. Likewise, the sequence of the operations of flow diagram 600 can be modified. It is appreciated that not all of the operations in flow diagram 600 may be performed. In various embodiments, one or more of the operations of method 600 can be controlled or managed by software, by firmware, by hardware or by any combination thereof, but is not limited to such. Method 600 can include processes of various embodiments of the present disclosure which can be controlled or managed by a processor(s) and electrical components under the control of computer or computing device readable and executable instructions or code (e.g., the optimizer model 150 of FIG. 1). The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory (e.g., like those found within the computing system 100 of FIG. 1).

At operation 602, a cyclotron (e.g., 402 or 502) generates and outputs a charged particle beam (e.g., 404 or 504). Note that operation 602 can be implemented in a wide variety of ways. For example, operation 602 can be implemented in any manner similar to that described and/or shown by the present disclosure, but is not limited to such.

At operation 604 of FIG. 6, the charged particle beam is modulated by a beam energy modulation apparatus (e.g., 406 or 508). It is noted that operation 604 can be implemented in a wide variety of ways. For example, operation 604 can be implemented in any manner similar to that described and/or shown by the present disclosure, but is not limited to such.

At operation 606, the beam modulation apparatus outputs the modulated charged particle beam to deliver a dosage to a target of a human patient in a fraction of a second (e.g., less than a second). Note that operation 606 can be implemented in a wide variety of ways. For example, operation 606 can be implemented in any manner similar to that described and/or shown by the present disclosure, but is not limited to such.

At operation 608 of FIG. 6, a computation can be made as to whether the treatment has been completed. If so, method 600 can end. However, if it is computed at operation 608 that the treatment has not been completed, method 600 can proceed to operation 602. Note that operation 608 can be implemented in a wide variety of ways. For example, operation 608 can be implemented in any manner similar to that described and/or shown by the present disclosure, but is not limited to such. In this manner, method 600 can perform energy modulation of a cyclotron beam for radiation therapy in accordance with various embodiments of the present disclosure.

The foregoing descriptions of various specific embodiments in accordance with the present disclosure have been presented for purposes of illustration and description. They are not intended to be exhaustive or to limit the present disclosure to the precise forms disclosed, and many modifications and variations are possible in light of the above teaching. The present disclosure is to be construed according to the Claims and their equivalents.

What is claimed is:

1. A radiation therapy system comprising:
a cyclotron that outputs a charged particle beam;
a first apparatus adapted to receive and decelerate said charged particle beam to produce a reduced energy charged particle beam, said first apparatus comprising a radio frequency structure;
a second apparatus adapted to receive and accelerate said charged particle beam to produce an increased energy charged particle beam, said second apparatus comprising a radio frequency structure; and
a set of switching dipoles adapted to receive and direct said reduced energy charged particle beam and said increased energy charged particle beam.

2. The radiation therapy system of claim 1, wherein said increased energy charged particle beam is adapted to deliver at least 4 grays (Gy) to a target in less than a second.

3. The radiation therapy system of claim 1, wherein said second apparatus further comprises a plurality of sequential radio frequency structures.

4. The radiation therapy system of claim 1, wherein said reduced energy charged particle beam is adapted to deliver at least 4 grays (Gy) to a target in less than a second.

5. The radiation therapy system of claim 1, wherein said charged particle beam comprises protons.

6. The radiation therapy system of claim 1, wherein said charged particle beam comprises carbon ions.

7. The radiation therapy system of claim 1, wherein said charged particle beam comprises helium nuclei.

8. The radiation therapy system of claim 1, wherein said first apparatus further comprises a plurality of sequential radio frequency structures.

9. A method comprising:
generating a charged particle beam with a cyclotron;
directing said charged particle beam to a first apparatus or a second apparatus;
if said first apparatus receives said charged particle beam, decelerating said charged particle beam with said first apparatus to produce a reduced energy charged particle beam, said first apparatus comprising a radio frequency structure;
if said second apparatus receives said charged particle beam, accelerating said charged particle beam with said second apparatus to produce an increased energy charged particle beam, said second apparatus comprising a radio frequency structure; and
directing said reduced energy charged particle beam or said increased energy charged particle beam with a set of switching dipoles.

10. The method of claim 9, wherein said increased energy charged particle beam is adapted to deliver at least 20 grays (Gy) to a target in a second.

11. The method of claim 9, wherein said reduced energy charged particle beam is adapted to deliver at least 40 grays (Gy) to a target in a second.

12. The method of claim 9, wherein said set of switching dipoles are coupled with said first and second apparatuses.

13. The method of claim 9, wherein said charged particle beam comprises protons.

14. The method of claim 9, wherein said charged particle beam comprises carbon ions.

15. The method of claim 9, wherein said charged particle beam comprises helium nuclei.

16. A radiation therapy system comprising:
an isochronous cyclotron that outputs a substantially fixed energy charged particle beam;
a decelerating apparatus adapted to receive and decelerate said substantially fixed energy charged particle beam to produce a reduced energy charged particle beam, said decelerating apparatus comprising a radio frequency structure;
an accelerating apparatus adapted to receive and accelerate said substantially fixed energy charged particle beam to produce an increased energy charged particle beam, said accelerating apparatus comprising a radio frequency structure; and
a set of switching dipoles adapted to receive and direct said reduced energy charged particle beam and said increased energy charged particle beam to a nozzle.

17. The radiation therapy system of claim 16, wherein said reduced energy charged particle beam or said increased energy charged particle beam is adapted to deliver greater than 40 grays (Gy) per second to a target.

18. The radiation therapy system of claim 16, wherein said substantially fixed energy charged particle beam comprises protons.

19. The radiation therapy system of claim 16, wherein said substantially fixed energy charged particle beam comprises carbon ions.

20. The radiation therapy system of claim 16, wherein said substantially fixed energy charged particle beam comprises alpha particles or helium nuclei.

* * * * *